United States Patent
Voellmy

(10) Patent No.: US 7,405,080 B2
(45) Date of Patent: Jul. 29, 2008

(54) COMPOSITIONS AND METHODS RELATING TO PREVENTION OF CHEMOTHERAPY-INDUCED ALOPECIA

(76) Inventor: Richard W. Voellmy, 701 Brickell Key Blvd., Apt. 801, Miami, FL (US) 33131

(*) Notice: Subject to any disclaimer, the term of this patent is extended or adjusted under 35 U.S.C. 154(b) by 0 days.

(21) Appl. No.: 09/939,161

(22) Filed: Aug. 24, 2001

(65) Prior Publication Data

US 2002/0001629 A1    Jan. 3, 2002

Related U.S. Application Data

(63) Continuation-in-part of application No. PCT/IB01/00422, filed on Mar. 21, 2001.

(60) Provisional application No. 60/191,580, filed on Mar. 23, 2000.

(51) Int. Cl.
*C12N 15/02* (2006.01)

(52) U.S. Cl. .......................... 435/450; 607/1; 424/450; 424/400

(58) Field of Classification Search .................. 424/450, 424/400; 607/1
See application file for complete search history.

(56) References Cited

U.S. PATENT DOCUMENTS 5,486,509 A * 1/1996 Jimenez et al. ............. 514/167
5,830,177 A * 11/1998 Li et al. ........................ 604/22

FOREIGN PATENT DOCUMENTS

| DE | 3724259 A1 | 2/1989 |
| WO | WO 98/15281 A1 | 4/1998 |
| WO | WO 98/46208 A1 | 10/1998 |

OTHER PUBLICATIONS

International Search Report for PCT/IB01/01607.

* cited by examiner

*Primary Examiner*—Michael G. Hartley
*Assistant Examiner*—Jim Rogers
(74) *Attorney, Agent, or Firm*—Saliwanchik, Lloyd & Saliwanchik

(57) ABSTRACT

The present invention relates to a method for protecting a human patient or a mammalian animal to be subjected to chemotherapy treatment of a tumor not residing in the scalp of the patient or the skin of the animal against chemotherapy-induced alopecia, comprising administering to the scalp of the patient or the skin of the animal an effective amount of a composition comprising a chemical inducer of the stress protein response sufficiently prior to the administration of a chemotherapeutic drug. It also relates to pharmaceutical compositions for the prevention of chemotherapy-induced alopecia. It further relates to a method for protecting a human patient or a mammalian animal to be subjected to chemotherapy treatment of a tumor not residing in the scalp of the patient or the skin of the animal against chemotherapy-induced alopecia, comprising administering to the scalp of the patient or the skin of the animal an effective heat dose sufficiently prior to the administration of a chemotherapeutic drug.

32 Claims, No Drawings

COMPOSITIONS AND METHODS RELATING TO PREVENTION OF CHEMOTHERAPY-INDUCED ALOPECIA

RELATED APPLICATIONS

This application is a continuation-in-part of international application PCT/IB01/00422 designating the United States filed on Mar. 21, 2001, which application claims priority to U.S. provisional application 60/191,580 filed on Mar. 23, 2000.

FIELD OF THE INVENTION

The invention relates to conditions and compositions capable of inducing the stress response in hair follicles and to methods of using said conditions and compositions for prevention of chemotherapy-induced alopecia.

BACKGROUND

Chemotherapy frequently induces hair loss. With chemotherapy, patients not only experience reduced stamina and independence but also must wear a physical symbol of their illness in the loss of their hair. This loss of hair is a traumatic experience that may well result in lower self-esteem and overall resistance. Some patients are known to have refused chemotherapy for fear of losing their hair. Scalp tourniquets have been used for several decades to prevent chemotherapy-induced alopecia. This technique involves the placement of a pneumatic tourniquet around the hairline at the time of administration of the chemotherapeutic drug. The tourniquet is then inflated to a pressure above the systolic arterial pressure, reducing blood flow to the scalp. The effectiveness of this technique has never been unambiguously demonstrated. The use of tourniquets has more or less been replaced by scalp hypothermia. With this technique, the scalp temperature is lowered to below 24° C. by application of cold packs, etc., prior to chemotherapy. The technique has been reported to afford a 50-70% good to excellent hair protective effect. However, results have remained notoriously variable. Furthermore, the practice is rather uncomfortable and is only tolerated for a short time. It is likely to be most effective for chemotherapy agents with short half lives. Moreover, several cases of scalp metastases in patients who used scalp hypothermia were reported. Finally, the technique appears to work considerably less well for combination chemotherapy than for therapy using single agents. Several pharmacological approaches for the prevention of chemotherapy-induced hair loss were also tested. For a review, see Dorr. 1998. Semin. Oncol. 25: 562-570. Most of the drugs tested failed (for example, alpha-tocopherol, minoxidil, calcitriol) or showed a marked sex preference (1,25-dihydroxy vitamin D3). More promising results were obtained with the immunomodulatory substance ammonium trichloro (dioxy-ethylene-0,0') tellurate (AS101). Sredni et al. 1996. Int. J. Cancer 65: 97-103. However, confirmation of this study is still being awaited. Furthermore, the question has to be resolved whether the immunomodulator is only effective if administered weeks prior to chemotherapy. If so, that would diminish somewhat the usefulness of the compound. Another drug candidate may be ImuVert, perhaps used in combination with acetylcysteine. ImuVert is a membrane vesicle-ribosome preparation from *Serratia marescens*. The combination of AS101 and acetylcysteine showed efficacy in a rodent model, but no human data are available. Some caution may be appropriate, since Imuvert as a biological response modifier has the potential of producing unacceptable toxicities. Thus, there is no drug on the market that generally protects against chemotherapy-induced alopecia, and there are only few drug candidates that are under active development. There is therefore a need for additional drug candidates and methods for protection against chemotherapy-induced alopecia.

SUMMARY OF THE INVENTION

Cells, tissues, organs and entire organisms respond to proteotoxic stress by enhancing the expression of a set of proteins that are termed heat shock or stress proteins (Hsps). This response is referred to herein as the stress protein response, and conditions and compounds that elicit this response are referred to as inducers. Conditions that elicit the response are specifically referred to as physical inducers, and compounds that elicit the response as chemical inducers. Based on what is currently known about the likely consequences of activation of the stress protein response in cancerous cells, tissues and organs, it is important to avoid activation of this response during chemotherapeutic treatment of cancer. The present invention is based on the realization by the inventor that there exists a particular situation, in which the protective effects of elevated levels of Hsps can be harnessed to prevent treatment-unrelated toxicity of chemotherapeutic drugs without compromising the efficacy of the same drugs viz-a-viz a tumor. This specific situation relates to the scalp hair of a patient undergoing chemotherapy treatment of a tumor not residing in the scalp or to the fur coat or parts thereof of a mammalian animal subjected to chemotherapy of a tumor not located in the skin. Many chemotherapeutic drugs and combinations of such drugs cause hair loss (alopecia) from the patient's scalp or from the animal's fur coat. A chemical inducer of the stress protein response can be applied to the scalp of a patient or to the skin of an animal such that it reaches the mitotically active cells of the hair follicles before entering the general circulation. As a consequence, the hair follicle cells and, depending on the nature of the composition comprising the chemical inducer, some other cells of the skin can be exposed to a concentration of chemical inducer that is sufficiently high to activate the stress protein response in these cells. Levels of stress proteins will increase, and, as a consequence, hair follicle cells will be protected against subsequent exposure to cytotoxic chemotherapeutic agents for a period of typically from 1-2 days, and the alopecia phenotype will not develop. While, inevitably, a fraction of chemical inducer molecules will eventually enter the general circulation, because of the high degree of dilution of chemical inducer in the circulation and because the stress protein response is not activated before a threshold concentration of chemical inducer is attained, activation of the stress response will be limited to cells of the hair follicles and, possibly, skin cells and will not occur to a significant extent in cells of the blood or other organs. Thus, topically administered chemical inducer will only activate the protective stress protein response in hair follicles and, possibly, in the skin but not elsewhere in the body and, consequently, will not negatively affect the efficacy of chemotherapy treatment of tumors not located in the scalp or skin. In the case of a chemotherapeutic regime in which a chemotherapeutic drug is only administered once, a single topical pretreatment of the patient or animal with a chemical inducer-comprising composition may suffice to produce the hair follicle-saving effect. Many chemotherapy regimes involve several cycles of treatment with chemotherapeutic drug which cycles may be days or weeks apart. In these cases topical administration of a composition comprising a chemical inducer can be similarly periodical, preceding each cycle of treatment with chemotherapeutic drug. With this type of regime, chemical inducer will be eliminated during each treatment cycle and will never accumulate to a level sufficient for systemic activation of the stress protein response.

Thus, the invention relates to a method for protecting a human patient or a mammalian animal to be subjected to chemotherapy treatment of a tumor not residing in the scalp of the patient or the skin of the animal against chemotherapy-induced alopecia. Protecting a human patient or a mammalian animal comprises preventing or reducing the severity of chemotherapy-induced alopecia. The method comprises administering to the scalp of the patient or the skin of the animal an effective amount of a composition comprising a chemical inducer of the stress protein response. Administration of chemotherapeutic drug is delayed for a sufficiently long time to permit induction of the stress protein response to take place and stress proteins in hair follicles to accumulate to protective levels. An effective amount of a composition comprising a chemical inducer is an amount that is at least equal to the amount required to cause a measurable increase in the concentration of at least one stress protein from the group of Hsps including Hsp90, Hsp70, Hsp25-27 and P-glycoprotein in hair follicles residing in skin exposed to the chemical inducer-comprising composition and that produces an increased resistance of the hair follicles to chemotherapeutic drugs. A measurable increase in the concentration of an Hsp is an increase of at least 25% over the concentration measured prior to administration of a composition of the invention. Exposure of cultured cells to a chemical inducer typically results in a rapid increase in Hsp expression and in a sufficient increase in Hsp concentrations within 2 to 12 hours to render cells resistant against toxicants including chemotherapeutic drugs. However, skin including hair follicles represents a significant barrier, and additional time, up to 24 hours, can be required for a chemical inducer to reach an effective concentration in hair follicle cells. Hence, chemotherapeutic drug is preferably administered between 2 and 36 hours after administration to the scalp of a patient or to the skin of an animal of a composition comprising a chemical inducer of the stress protein response. More preferably, administration of chemotherapeutic drug is delayed by 8 to 24 hours. Many chemical inducers of the stress protein response are known. Generally, any compound that produces some measure of proteotoxicity functions as a chemical inducer. Preferred inducers are compounds of the benzoquinone ansamycin series (e.g., geldanamycin), arsenic salts (e.g., sodium arsenite), tin salts (e.g., stannous chloride), zinc salts (e.g., zinc chloride) and diamide. A further preferred chemical inducer is an activated heat shock transcription factor 1 (HSF1) that may be administered as a recombinant protein or as a nucleic acid containing a gene for the factor in an expressible form.

The method of the invention also encompasses pretreatment of the scalp of a patient or the skin of an animal with compositions that comprise a chemical inducer and additionally a penetration enhancer to facilitate transport of inducer to the cells of the hair follicles.

The invention also relates to pharmaceutical compositions for protection against chemotherapy-induced alopecia, the compositions comprising a chemical inducer of the stress protein response, a penetration enhancer and an appropriate diluent or solvent. Preferred chemical inducers used in these compositions are diamide, compounds of the benzoquinone ansamycin series, arsenic salts, tin salts, zinc salts and activated HSF in protein or nucleic acid form.

The invention further relates to the use of a chemical inducer of the stress protein response for the manufacture of a medicament for protecting a human patient or a mammalian animal to be subjected to chemotherapy treatment of a tumor not residing in the scalp of the patient or the skin of the animal against chemotherapy-induced alopecia, an effective amount of which medicament is administered to the scalp of the human patient or the skin of the mammalian animal sufficiently prior to administration of chemotherapeutic drug. An effective amount of such medicament is an amount that is at least equal to the amount required to cause a measurable increase in the concentration of at least one stress protein from the group of Hsps including Hsp90, Hsp70, Hsp25-27 and P-glycoprotein in hair follicles residing in skin exposed to the chemical inducer-comprising medicament and that produces an increased resistance of the hair follicles to chemotherapeutic drugs. A measurable increase in the concentration of an Hsp is an increase of at least 25% over the concentration measured prior to administration of a medicament of the invention. Preferably, chemotherapeutic drug is administered between 2 and 36 hours after administration to the scalp of a patient or to the skin of an animal of a medicament comprising a chemical inducer of the stress protein response. More preferably, administration of chemotherapeutic drug is delayed by 8 to 24 hours. Many chemical inducers of the stress protein response are known. Generally, any condition or compound that produces some measure of proteotoxicity functions as an inducer. Preferred chemical inducers for use in the manufacture of a medicament of the invention are compounds of the benzoquinone ansamycin series (e.g., geldanamycin), arsenic salts (e.g., sodium arsenite), tin salts (e.g., stannous chloride), zinc salts (e.g., zinc chloride) and diamide. An additional preferred chemical inducer is an activated heat shock transcription factor 1 (HSF1) that may be administered as a recombinant protein or as a nucleic acid containing a gene for the factor in an expressible form. Also encompassed by the invention is the use of a chemical inducer of the stress protein response and of a penetration enhancer facilitating delivery of inducer to hair follicles for the manufacture of a medicament for protecting against chemotherapy-induced alopecia.

The invention also relates to a method using a physical inducer of the stress protein response, e.g., heat, for protecting a human patient or a mammalian animal to be subjected to chemotherapy treatment of a tumor not residing in the scalp of the patient or the skin of the animal against chemotherapy-induced alopecia. Protecting a human patient or a mammalian animal comprises preventing or reducing the severity of chemotherapy-induced alopecia. In one embodiment, the method comprises administering to the scalp of the patient or the skin of the animal an effective heat dose. Administration of chemotherapeutic drug is delayed for a sufficiently long time to permit induction of the stress protein response to take place and stress proteins in hair follicles to accumulate to protective levels. An effective heat dose is a dose at least equal to the dose required to cause a measurable increase in the concentration of at least one stress protein from the group of Hsps including Hsp90, Hsp70, Hsp25-27 and P-glycoprotein in hair follicles residing in skin exposed to the heat dose and that produces an increased resistance of the hair follicles to chemotherapeutic drugs. A measurable increase in the concentration of an Hsp is an increase of at least 25% over the concentration measured prior to administration of a composition of the invention. Exposure of cultured cells to a heat dose typically results in a relatively rapid increase in Hsp expression and in a sufficient increase in Hsp concentrations within 2 to 24 hours to render cells resistant against toxicants including chemotherapeutic drugs. Hence, chemotherapeutic drug is preferably administered between 2 and 24 hours after administration to the scalp of a patient or to the skin of an animal of a heat dose. More preferably, administration of chemotherapeutic drug is delayed by 6 to 12 hours. Heat can be administered by several different means. Contact of the scalp of a patient or the skin of an animal in need of treatment with a heated surface or with a heated liquid (e.g., water) will provide a heat dose to the skin and the hair follicle cells. Other means for heating skin and hair follicle cells include exposure to ultrasound, or to microwave, infrared or radiofrequency radiation.

Accordingly, the embodiments of the invention described herein also relate to a method for the treatment of cancer in a human patient or a mammalian animal in need thereof, comprising (a) administering to the scalp of the patient or the skin of the animal an effective dose of a physical inducer such as heat or an effective amount of a composition comprising a chemical inducer of the stress protein response and (b) subjecting said human patient or animal to chemotherapy treatment.

DETAILED DESCRIPTION

Hair consists of the hair root, the hair bulb (the germinative center) and the hair shaft. Cells proliferate in the hair bulb, and the hair is pushed from the root through the scalp. The final product is a strand of tightly compacted keratin. Hair growth occurs in three phases. The first phase is the anagen phase, which is the growth phase. 85-90% of human hair follicles are in the anagen phase. Each hair follicle comprises a bulbous base of mitotically active matrix cells. From these all cells of the hair shaft differentiate and grow. Cells move up in rows to the upper bulb and elongate vertically. Finally, they are being forced upwards and emerge at the skin surface. Human hair bulb cells divide on the average every 12 to 24 hours. Because of this substantial mitotic activity, the hair bulb cells are particularly susceptible to cytotoxic agents. The anagen phase lasts between two and six years in humans. The second stage is the catagen phase, which lasts a few weeks in humans. In this phase the hair root is separated from the hair bulb, pigment storage is terminated, and the root end is pushed out from the bulb. Less than 1% of human hair is in the catagen phase. The third phase is the telogen phase, which is characterized by a lack of mitotic activity. This phase lasts between three and six months. About 10% of human hair is in the telogen phase. Dorr. 1998. Semin. Oncol. 25: 562-570. Hussein. 1993. South. Med. J. 86: 489-496.

Alopecia or hair loss is frequently associated with cancer chemotherapy. Dorr. 1998. Semin. Oncol. 25: 562-570. Many of the commonly used chemotherapeutic drugs induce hair loss, although there appear to be differences in the ability of different drugs to cause alopecia. Most severe effects are produced by cyclophosphamide, daunorubicin, docetaxel, doxorubicin, etoposide, ifosfamide, paclitaxel, teniposide and topotecan. Joss et al. 1988. Recent Res. Cancer Res. 108: 117-126. Perry (ed). The Chemotherapy Source Book, Baltimore, Md., Williams & Wilkins, 1996, pp. 293-555, 595-606. Somewhat less effective in inducing hair loss are actinomycin, 5-fluorouracil, hydroxyurea, methotrexate, mitomycin, mitoxantrone, nitrogen mustard, vinblastine, vincristine, vindesine and vinorelbine. Oftentimes, these cytotoxic, chemotherapeutic drugs are used in combination, which increases the risk of alopecia over that inherent in the individual drugs.

There has been relatively little research to identify the actual mechanism(s) of chemotherapy-induced alopecia. Presumably, this is due to the fact that the hypothesis that cytotoxic agents kill hair follicle cells by the same mechanism by which they kill cancer cells and other proliferating cells is immediately plausible. Nevertheless, doxorubicin was shown to kill hair cells by setting off an apoptotic mechanism. Cece. 1996. Lab. Invest. 75: 601-609. The same study also discovered that the targets of doxorubin toxicity were matrix and upper bulb cells of the hair follicle. Another study reported that cyclophosphamide induced massive apoptosis in anagen hair follicles. Schilli et al. 1998. J.Invest.Dermatol. 111: 598-604.

Theoretically, there would appear to be several ways to prevent chemotherapy-induced hair loss, namely (1) reduction of the amount of chemotherapeutic agent delivered to the bulb, (2) local inactivation of the chemotherapeutic drug, and (3) protection of bulb cells as proposed by the invention disclosed herein. The present invention relates to deliberate localized induction of the stress protein response in the scalp of a patient or the skin of a mammalian animal in need of chemotherapy to protect hair follicles against the cytotoxic effects of chemotherapeutic agents and combinations thereof without compromising the therapeutic efficacy of the latter agents.

Cells in every organ and every tissue respond to proteotoxic stress by enhancing the expression of so called heat shock or stress proteins (Hsps). This response is being referred to herein as the stress protein response. For reviews, see Voellmy. 1994. Crit.Rev.Eukaryotic Gene Expr. 4: 357-401. Voellmy. 1996. In: Stress-Inducible Cellular Responses (Feige et al. eds.), Birkhauser Verlag, Basel, Switzerland, pp.121-137. Parsell and Lindquist. 1993. Annu.Rev.Genet. 27: 437-496. Historically, the term "Hsp" was used to describe those proteins whose rates of synthesis were increased in cells exposed to the prototypic stressor heat. Hsps were distinguished based on their subunit molecular weights. Major Hsps have subunit sizes of about 110, 90, 70, 60, 20-30, and 10 kDa, respectively, and are referred to as Hsp110, Hsp90, Hsp70, Hsp60, Hsp20-30 (or small Hsp) and Hsp10, respectively. It is now known that most of these Hsps are molecular chaperones that assist folding and refolding of proteins, intracellular trafficking of proteins, assembly and dissociation of protein complexes, protein degradation, etc. Stress proteins are also known to participate in the regulation of the activity and stability of important cellular regulatory proteins such as steroid hormone receptors, certain signaling kinases including Raf and Ras, and telomerase. In agreement with their physiological functions, Hsps are not only prevalent in stressed cells but also in unstressed cells. Certain Hsps are major proteins even in the unstressed cell. For example, Hsp90 represents 1-2% of total cellular protein in the absence of stress. When cells are stressed, concentrations of Hsps increase further.

It was long known that most Hsps are encoded by families of highly related genes. While some of these genes are strictly stress-regulated, others are already substantially active in the unstressed cell. Some of the genes are not stress-regulated at all and express stress protein at all times. The latter genes are also referred to as cognate stress protein genes, and the proteins encoded by them as stress or heat shock cognate proteins (Hscs as opposed to Hsps). The best known family of stress protein genes encodes proteins with subunit molecular weights of about 70 kDa (Hsp/c70). Humans possess an hsp70 gene that is already substantially active in the unstressed cell, and whose activity is increased by about 10 fold during heat stress. This gene is also known as the hsp70A gene. There are at least two other genes, referred to as hsp70B and hsp70B' genes, that are strictly heat-regulated. Their activity increases by about 1000 fold in the heat-stressed cell. Human cells also have at least one hsc70 gene encoding a protein that is highly related to Hsp70. This gene is essentially not stress-regulated.

As discussed before, the activity of stress-regulatable hsp genes is increased when the cell is exposed to a proteotoxic stress. Such proteotoxic stress may be induced, for example, by heat, UV light, electromagnetic field, heavy metal ions such as a Cd, Zn, Sn, or Cu ions, other sulfhydryl-reactive compounds such as sodium arsenite (an arsenic salt), inhibitors of energy metabolism, in particular inhibitors of mitochondrial function, amino acid analogs such as canavanine or azetidine carboxylate, protein denaturants such as ethanol, oxidizing agents such as diamide (diazinedicarboxylic acid bis(N,N-dimethylamide)) or other agents including, for example, toxicants that form protein adducts such as acetaminophen. The activity of hsp genes is also elevated in cells exposed to inhibitors of proteolysis such as lactacystin or to compounds that interfere with the proper function of a stress protein. Examples for the latter type of compound are the benzoquinone ansamycins including geldanamycin and herbimycin A that are known to specifically bind Hsp90 in its nucleotide-binding site. The current model that appears to be generally accepted in the field holds that exposure to any of these stresses results in an increased rate of protein unfolding and, consequentially, in an elevated concentration of nonnative protein. A sufficiently elevated level of nonnative protein triggers increased expression of hsp genes. Quantitative measurements suggested that substantially increased hsp gene activity requires denaturation of about 1-2% of cellular protein. Because exposure to the above chemicals or physical conditions results in increased hsp gene activity, these chemicals or physical conditions are also referred to as chemical or physical inducers of the stress protein response. Chemical as well as physical inducers can be used for the practice of the present invention.

The stress regulation of hsp genes is mediated by a heat shock transcription factor (HSF). Mammalian cells express several different but related HSF molecules. Only one of these factors, HSF1, appears to be normally involved in the stress regulation of hsp genes. HSF1 is a ubiquitously expressed factor that is inactive, i.e., incapable of transactivating an hsp gene, in the unstressed cell. When the cell is exposed to one of the above-described inducers, the factor is activated and acquires transactivation ability. In the unstressed cell, HSF1 forms part of a dynamic heterooligomeric complex that includes Hsp90 and, possibly, other chaperones and co-factors. Zou et al. 1998. Cell 94: 471-480. When the cell is stressed, nonnative proteins accumulate. These nonnative proteins bind preferentially Hsp90 and other chaperones, competing with HSF1 for binding the same chaperones. As a result of this competition, a fraction of HSF1 is no longer chaperone-bound. Unassociated HSF1 rapidly homotrimerizes and, as a consequence, acquires the ability to specifically bind so called heat shock element (HSE) sequences present in promoters of hsp genes. It appears that for full activation HSF1 further needs to be hyperphosphorylated. Recent unpublished observations raise the possibility that activating phosphorylation events may be negatively regulated by binding of chaperone complexes to the trimeric transcription factor.

Mutagenesis studies of human HSF1 led to the discovery of mutant factors that are no longer stress-regulated but are capable of transactivating hsp genes in the absence of any stress. Zuo et al. 1995. Mol.Cell.Biol. 15: 4319-4330. Xia et al. 1999. Cell Stress & Chaperones 4: 8-18. These mutant factors that function as chemical inducers of the stress protein response are also referred to herein as activated HSF1. Deletions and amino acid substitutions in the region between about amino acids 185 and 315 of the 529-residue-long human HSF1 polypeptide result in this deregulated phenotype. Deletions and substitutions in the region between about amino acids 200 and 315 are known to be constitutively transactivating when overexpressed from transfected genes. Of particular interest are substitutions and deletions in the region between about amino acids 185 and 200 which yield factors that are constitutively active even at exceedingly low concentrations. Examples of deletions and substitutions known to render HSF1 constitutively transactivating were described in patent application PCT/US98/01038 (WO98/31803) which is incorporated herein in its entirety by reference. It is noted that application WO98/31803 also described nonhuman HSF and chimeric factors capable of transactivating hsp genes in the absence of stress. While not every deletion or substitution in the residue-185-315 region will result in a deregulated human HSF1, the identification of deregulated mutant factors is readily achieved by a person skilled in the art, using one of several methods of analysis. For example, a gene encoding a mutated HSF1 to be tested may be inserted in a suitable expression vector. The resulting expression construct may be introduced by transfection in a cell containing one or more copies of an hsp promoter-driven reporter gene. An example of such a cell line is HeLa-CAT, a human cell line containing several copies of a chloramphenicol acetyltransferase gene under the control of a human hsp70B promoter. Baler. et al. 1992. J.Cell Biol. 117: 1151-1159. Increased reporter gene activity which can be measured by a convenient assay of reporter activity will indicate that a mutated HSF1 is capable of transactivating an hsp gene in the absence of stress.

Exposure of cells to a nonlethal heat stress was long known to protect the cells against a subsequent more severe heat stress that is lethal to naive cells. Parsell and Lindquist. 1993. Annu.Rev.Genet. 27: 437-496. Heat pretreatment also protects cells against certain chemical stresses. This protective effect is correlated with increased expression of Hsps. Transfection experiments provided direct evidence that increased levels of certain individual stress proteins produce stress tolerance. For example, cells transfected to transiently overexpress Hsp70 or cell lines stably overexpressing the same Hsp were found to have an increased stress resistance. Li et al. 1991. Proc.Natl.Acad.Sci USA 88: 1681-1685. Huot et al. 1991. Cancer Res. 51: 5245-5252. Jaattela et al. 1992. EMBO J. 11: 3507-3512. Analogous observations were made in animal experiments. The ability of Hsps to protect against ischemia/reperfusion damage in the heart was demonstrated by heat preconditioning experiments (Liu et al. 1992. Circulation 86: 11358-11363. Richard et al. 1996. Fund.Clin.Pharmacol. 10: 409-415. Joyeux et al. 1998. Cardiovasc.Res. 40: 124-130) as well as by studies using transgenic animals. In the latter studies, hearts of transgenic mice overexpressing Hsp70 were subjected to an ischemic event. Recovery of the hearts from ischemic trauma was assessed following 30 minutes of reperfusion after the ischemic event. As judged from measurements of contractile force and creatine kinase release, hearts from transgenic mice showed a significant improvement of recovery when compared to hearts from non-transgenic animals. Plumier et al. 1995. J.Clin.Invest. 95: 1854-1860. Marber et al. 1995. J.Clin.Invest. 95: 1446-1456. Similar results were obtained in experiments in which hearts of adult rats were transfected with an hsp70 gene by intracoronary infusion of an HVJ-liposome formulation containing the hsp70 gene. Suzuki et al. 1997. J.Clin.Invest. 99: 1645-1650. Transgenic mice overexpressing Hsp70 in the brain also exhibited reduced neural damage following middle cerebral artery occlusion. Plumier et al. 1997. Cell Stress & Chaperones 2: 162-167. Preconditioning of rabbits with heat or a tin salt was found to prevent paralysis caused by acute spinal cord ischemia. Perdrizet et al. 1999. Ann.N.Y.Acad.Sci. 874:

320-325. Personal commununication. Similarly, protection of kidney function from ischemic damage was demonstrated in a pig model. Perdrizet et al. 1999. Ann.N.Y.Acad.Sci. 874: 320-325.

Regarding protective effects of stress proteins in the skin, it was demonstrated repeatedly that heat preconditioning increases the survival of skin flaps. This enhanced survival correlated with increased expression of Hsp70 in the skin flaps. Koenig et al. 1992. Plast.Reconstr.Surg. 90: 659-694. Wang et al. 1998. Plast.Reconstr.Surg. 101: 776-784. Furthermore, heat preconditioning protected keratinocyte and epithelial cell cultures against UVB-induced damage. This protective effect was associated with elevated Hsp levels, in particular Hsp70 levels. Trautinger et al. 1995. J.Invest.Dermatol. 105: 160-162. Injection of an Hsp70 antibody increased the sensitivity of keratinocytes to UVB injury. Bayerl and Jung. 1999. Exp.Dermatol. 8: 247-253.

Cells expressing a constitutively active HSF1 mutant overexpressed Hsps and exhibited increased resistance to heat stress, simulated ischemia and exposure to cyclophosphamide (tested in hepatocyte-derived (HepG2) cells). Xia et al. 1999. Cell Stress & Chaperones 4: 8-18. Overexpression of stress protein Hsp70 enhanced cellular resistance to adriamycin. Roigas et al. 1998. Prostate 34: 195-202. Overexpression of Hsp27 also resulted in resistance to doxorubicin. Richards et al. 1996. Cancer Res. 56: 2446-2451. Oesterreich et al. 1993. Cancer Res. 53: 4443-4448. Karlseder's laboratory and others similarly reported that specific overexpression of Hsp70 or Hsp27 protected cells against doxorubicin-induced apoptosis. Karlseder et al. 1996. Biochem.Biophys.Res. Commun. 220: 153-159. Richards et al. 1996. Cancer Res. 56: 2446-2451. Oesterreich et al. 1993. Cancer Res. 53: 4443-4448. Hsp70 or Hsp27 overexpression also rendered cells resistant to cisplatin. Komatsuda et al. 1999. Nephrol.Dial.Transplant. 14: 1385-1390. Richards et al. 1996. Cancer Res. 56: 2446-2451. Oesterreich et al. 1993. Cancer Res. 53: 4443-4448. These studies demonstrated clearly that increased expression of individual Hsps results in protection of particular cell types from the toxicity of cytotoxic chemotherapeutic agents. Because of the conserved structure and function of stress proteins and the conservation of the stress protein response, it is expected that the latter findings similarly apply to other cell types than those studied as well as to cells in tissues. It is further expected that overexpression of Hsps will also protect cells against other cytotoxic agents than those tested in the above studies and that overexpression of the entire cohort of Hsps will have at least a comparable protective effect than overexpression of individual Hsps. Finally, several studies supported the notion that activation of the stress protein response also induces multidrug resistance. Chin et al. 1990. J.Biol.Chem. 265: 221-6. Kim et al. 1998. Exp.Mol.Med. 30: 87-92. These findings suggest that activation of the stress protein response will diminish the efficacy of cytotoxic chemotherapeutic drugs used alone or in combination in cancer chemotherapy. Thus, activation of the stress protein response during cancer chemotherapy treatment is clearly counterindicated.

The protective effect of an activated stress protein response on cancer cells may be diminished somewhat by other mechanisms. Continued overexpression of a constitutively active HSF1 inhibited cell growth. Xia et al. 1999. Cell Stress & Chaperones 4: 8-18. Growth-arrested cells may be less susceptible to cytotoxic agents than growing cells. However, it appeared that growth arrest of activated HSF1-overexpressing cells was due to the effective redirection of these cells towards production of excessive amounts of Hsps in lieu of other essential proteins. It is doubtful that this situation is physiologically relevant. Hsps have a privileged relationship with the immune system. In the late 1980s, a number of investigators realized that Hsps were preferred targets for humoral and cellular immune responses to infection by bacteria, fungi and protozoa. These findings were puzzling because stress proteins even from divergent organisms are highly related. Hence, autoimmune reactions may occur. Indeed, infected, vaccinated and even healthy patients express antibodies and T-cells directed against stress proteins. Apparently, immune responses against stress proteins are finely tuned, and severe autoimmune reactions are avoided. More recently it was discovered that stress proteins drastically enhance the immunogenicity of covalently and non-covalently linked antigens. Interestingly, and this distinguishes stress proteins from most other adjuvants, stress protein-enhanced immunity appears to be predominantly of a Th1-like type, stimulating phagocytes and activation of cytotoxic lymphocytes (CTL). Huang et al. 2000. J.Exp.Med., in press. While the underlying mechanism for the immunological activity of stress proteins is not well understood, it is suspected that it may involve stimulation of antigen presentation. Over the last few years, several studies were published suggesting that increased expression of stress proteins alone may enhance presentation by tumor cells of their antigens and, hence, may stimulate immune responses directed against the tumor cells. Melcher et al. 1998. Nat.Med. 4: 581-587. Todryk 1999. J.Immunol. 163: 1398-1408. Wells et al. 1997. Scand. J.Immunol. 45: 605-612. However, while anti-tumor activity of preparations containing stress proteins complexed with antigenic peptides/proteins could be demonstrated in tumor models, the importance of effects affecting the immune system resulting from overexpression of stress proteins within tumor cells remains uncertain. It seems unlikely that the latter effects would be capable of canceling out the cytoprotective effects of overexpressed stress proteins, which cytoprotective effects will diminish the efficacy of chemotherapy treatment.

Thus, based on what is currently known about the likely consequences of activation of the stress protein response in cancerous cells, tissues and organs, it is critically important to avoid activation of the stress protein response during chemotherapy treatment of cancer. The present invention is based on the realization by the inventor that in at least one particular situation it is possible to harness the protective activity of elevated levels of Hsps to prevent treatment-unrelated toxicity of chemotherapeutic drugs without compromising the efficacy of the drugs viz-a-viz the cancer in need of chemotherapy treatment. This situation concerns the hair follicles in the scalp of a cancer patient or in the skin of an animal in need of chemotherapy. As discussed before, treatment-unrelated toxicity of many chemotherapeutic drugs and combinations of drugs results in loss of scalp hair in a human patient and in loss of hair from the fur coat of treated animals. A chemical inducer of the stress protein response can be administered directly to the scalp of a cancer patient or the skin of an animal such that it reaches the mitotically active cells of the hair follicles prior to entering circulation, i.e., without much dilution. Levels of stress proteins in inducer-exposed hair follicle cells and, possibly, some other cells of the skin will increase, and, within a few hours, hair follicles will be protected against subsequent exposure to cytotoxic chemotherapeutic agents for a period of typically from 1-2 days. Eventually, a fraction of the inducer molecules will enter the blood stream. However, because of the high level of dilution of chemical inducer in the blood stream, and because chemical inducer needs to attain a threshold concentration before a stress protein response is mounted, activation of the stress protein response will remain limited to cells of the hair follicles and, possibly, of the skin and will not occur to a significant extent in cells of the blood or other organs. Hence, chemical inducer will never reach but a negligible systemic concentration, which concentration is too low to affect the efficacy of chemotherapy treatment of tumors not residing in hair follicles or, if topically administered chemical inducer is not specifically targeted to hair follicles, in skin exposed to inducer. Because chemotherapy regimes frequently involve several cycles of administration of chemotherapeutic drugs days or weeks apart, administration of chemical inducer can also be periodical, preceding each cycle of administration of chemotherapeutic drugs. Even if administered repeatedly, with this type of administration regime chemical inducer will be eliminated during each treatment cycle and will never accumulate to levels sufficient for systemic activation of the stress protein response. Thus, the present invention involves the topical administration of an effective amount of a chemical inducer of the stress protein response to the scalp of a cancer patient or the skin of an animal sufficiently prior to the administration of a chemotherapeutic agent to treat a cancer not residing in inducer-exposed cells to selectively activate a protective stress protein response in the scalp of the patient or the skin of the animal. A chemical inducer may also be topically administered to any other region of the human body susceptible to chemotherapy-induced alopecia, such as for example eyebrow, beard and mustache regions. Furthermore, it is also expected that the methods and compositions of the invention will also be effective for the protection against alopecia caused by radiation treatment. Thus, the invention also encompasses any of the embodiments described for the protection of a human patient or animal from radiation-induced alopecia. As used herein, an "effective amount" refers to amount of a chemical inducer (or inducer-comprising composition) that will elicit the biological response of hair follicles of a human patient or animal or the medical response of a human patient or animal that is being thought by a researcher or clinician. The term "effective amount" comprises any amount which, as compared to a corresponding hair follicle-containing tissue or human or animal subject which has not received such amount, results in increased resistance of hair follicles against killing by chemotherapeutic agents or in improved treatment, prevention, or severity reduction of chemotherapy-induced alopecia.

Alternatively, a physical inducer of the stress protein response such as transient heat can be targeted directly to the scalp of a cancer patient or the skin of an animal such that it reaches the mitotically active cells of the hair follicles but does not penetrate much below the skin. Levels of stress proteins in inducer-exposed hair follicle cells and other cells of the skin will increase, and, within a few hours, hair follicles will be protected against subsequent exposure to cytotoxic chemotherapeutic agents for a period of typically from 1-2 days. Because of the targeted administration of the physical inducer, stress protein levels will not increase in other cells than skin cells, and the efficacy of chemotherapy treatment of tumors not residing in hair follicles or other skin locations will not be diminished. Because chemotherapy regimes frequently involve several cycles of administration of chemotherapeutic drugs days or weeks apart, administration of physical inducer can also be periodical, preceding each cycle of administration of chemotherapeutic drugs. Thus, the present invention also involves the targeted administration of an effective dose of a physical inducer of the stress protein response to the scalp of a cancer patient or the skin of an animal sufficiently prior to the administration of a chemotherapeutic agent to treat a cancer not residing in inducer-exposed cells to selectively activate a protective stress protein response in the scalp of the patient or the skin of the animal. A physical inducer may also be targeted to any other region of the human body susceptible to chemotherapy-induced alopecia, such as for example eyebrow, beard and mustache regions. Furthermore, it is expected that this embodiment of the methods of the invention will also be effective for the protection against alopecia caused by radiation treatment. Thus, the invention also encompasses any of the embodiments described for the protection of a human patient or animal from radiation-induced alopecia. As used herein, an "effective dose" refers to a dose of a physical inducer that will elicit the biological response of hair follicles of a human patient or animal or the medical response of a human patient or animal that is being thought by a researcher or clinician. The term "effective dose" comprises any dose which, as compared to a corresponding hair follicle-containing tissue or human or animal subject which has not received such dose, results in increased resistance of hair follicles against killing by chemotherapeutic agents or in improved treatment, prevention, or severity reduction of chemotherapy-induced alopecia.

Inducers

As discussed before, inducers of the stress protein response include physical inducers such as heat, UV radiation, electromagnetic field and chemical inducers such as heavy metal ions, e.g., Cd, Zn, Sn or Cu ions, other sulfhydryl-reactive compounds, e.g., sodium arsenite (an arsenic salt), inhibitors of energy metabolism, in particular inhibitors of mitochondrial function, amino acid analogs, e.g., canavanine or azetidine carboxylate, protein denaturants, e.g., ethanol and guanidinium hydrochloride, oxidizing agents, e.g., diamide, and other agents, e.g., toxicants that form protein adducts such as acetaninophen. Inducers also include inhibitors of proteolysis such as lactacystin and compounds that interfere with the proper function of an Hsp. Examples of the latter type of compound include benzoquinone ansamycins such as geldanamycin and herbimycin A that are known to specifically bind Hsp90 in its nucleotide-binding site. For a list of typical inducers see Zou et al. 1998. Cell Stress & Chaperones 3: 130-141. The above list is not exhaustive. Many additional chemicals are also known to be inducers of the stress protein response. Some of these chemicals including biclomol, cyclopentenones and certain prostaglandins do not appear to fit into any of the above-cited groups. Furthermore, there is little doubt that new chemical inducers will be discovered in the future, because, generally, any compound that has some degree of proteotoxicity will induce the stress protein response. Whether a particular compound will be proteotoxic may or may not be readily deduced from its structure. It seems therefore more appropriate to define chemical inducers functionally rather than structurally. For the purposes of this invention an inducer is a compound that is capable of enhancing Hsp expression at a sublethal concentration or is a sublethal physical condition that stimulates Hsp expression. There are many methods for discovering whether or not a compound/physical condition is an inducer. For example, parallel mammalian cell cultures can be exposed to a range of sublethal concentrations of a substance to be tested in the presence of a radiolabeled amino acid. After an appropriate exposure period, cells are harvested and lysed, and cell lysates are subjected to SDS-PAGE and autoradiography or fluorography. If the substance tested is a chemical inducer, it will enhance the rate of synthesis of polypeptides with molecular weights typical for Hsps (e.g., 90,70, 25-27 kDa). In a more rigorous version of the same test, a particular Hsp is immunoprecipiated from the cell lysates using an anti-Hsp antibody, and the relative rate of synthesis of the Hsp is estimated from SDS-PAGE and autoradiography or fluorography of immunoprecipitated protein. Anti-Hsp antibodies are commercially available, for example, from StressGen Biotechnologies Corp. of Victoria, B.C.

Note that not only small molecule compounds such as those discussed before are chemical inducers of the stress protein response. Chemical inducers also include larger molecules such as proteins and nucleic acids. Nonlimiting examples of such chemical inducers are functional genes encoding a constitutively active HSF1 as well as constitutively active HSF1 proteins. Their delivery to cells will induce stress protein expression that can be detected by the test described before. Also included are genes for individual stress proteins such as Hsp90, Hsp70, Hsp25-27 and P-glycoprotein and the proteins encoded by these genes. Their delivery to cells will partially reproduce the stress protein response, i.e., result in an increased level of a particular stress protein that can be detected by the above test.

Embodiments of the present invention involve topical administration of a composition comprising a chemical inducer of the stress protein response to the scalp of a cancer patient or the skin of a mammalian animal. Because of this mode of administration, the systemic concentration of chemical inducer remains low. Consequently, there is relatively little danger of systemic or organ-specific toxicity caused by a chemical inducer. It would therefore appear that essentially any chemical inducer can be used in the compositions of the invention. Most preferred, however, will be chemical inducers that have already been tested or used in humans such as, for example, tin salts, zinc salts and arsenic salts, or chemical inducers that are about to be tested in humans such as, for example, a benzoquinone ansamycin. Also preferred are chemical inducers with well known chemical reactivity such as diamide as well as chemical inducers that are expected to be highly specific activators of the stress protein response such as an activated form of HSF1 delivered as nucleic acid or protein.

Formulations Comprising a Chemical Inducer and Delivery

Depending on its chemical properties (e.g., lipophilicity, molecular size), a chemical inducer may be topically administered in a solvent such as ethanol, propylene glycol or glycerol. Schilli et al. 1998. J.Invest.Dermatol. 111: 598-604. Tata et al. 1994. J.Pharm.Sci. 83: 1508-1510. Sredni et al. 1996. Int.J.Cancer 65: 97-103. More typically, a chemical inducer will be administered in a formulation that also includes one or more penetration enhancers (or promoters). Dermal and intrafollicular delivery are highly active fields of academic and industrial research, and a person skilled in these arts will know of appropriate methods for delivering a particular chemical inducer. The term "penetration enhancer (or promoter)" is used here in its broadest sense to include any physical method or any chemical composition that increases the permeability of the skin by temporarily compromising the integrity and physicochemical properties of the skin or that results in selective targeting of hair follicles. It is also meant to include delivery vehicles such as liposomes, including deformable and ultradeformable liposomes, as well as active electric methods such as iontophoresis, ultrasonic vibration and electroporation. It also includes the preparation of lipophilic derivatives of molecules to be delivered. For example, tape stripping was used to enhance the permeability of skin, particularly to macromolecules. Yang et al. 1995. Br.J.Dermatol. 133: 679-685. Repeated brushing of skin permitted efficient delivery even of naked DNA into the outer layers of the epidermis and hair follicles. Yu et al. 1999. J.Invest.Dermatol. 112: 370-375. Well known chemical penetration enhancers are Azone, DegammaE, or n-decylmethyl sulphoxide. Hoogstraate et al. 1991. Int.J.Pharm. 76: 37-47. Bodde et al. 1989. Biochem.Soc.Trans. 17: 943-945. Choi et al. 1990. Pharm.Res. 7: 1099-1106. See also Marjukka Suhonen et al. 1999. J.Controlled Release 59: 149-161. Recent examples of chemical permeation enhancers are N-acetylprolinate esters, polyethylene glycol-8-glyceryl caprylate/caprate, SEPA and hydrogels such as deoxycholate-hydrogels. Tenjarla et al. 1999. Int.J.Pharm. 192: 147-158. Tran. 1999. J.Surg.Res. 83: 136-140. Diani et al. 1995. Skin Pharmacol. 8: 221-228. Valenta et al. 1999. Int.J.Pharm. 185: 103-111. Lipophilic derivatization of molecules to be delivered has been successful, for example, in the case of IFNalpha. Acyl derivatives (chain length 12-16) showed much increased cutaneous and percutaneous absorption than the underivatized molecule. Foldvari et al. 1999. Biotechnol.Appl.Biochem. 30: 129-137. Iontophoresis is a method based on electrical stimulation of skin permeability for mostly ionized molecules. It has been used successfully to deliver in the skin small molecules as well as small polypeptides. Guy. 1998. J.Pharm.Pharmacol. 50: 371-374. One of the latest electrical methods is electroporation that has been used to deliver hydrophilic compounds in the skin. Banga and Prausnitz. 1998. Trends Biotechnol. 16: 408-412. Methods for delivering nucleic acids to hair follicles are also available. WO 00/24895 and WO 98/46208.

The use of encapsulation technologies for skin delivery and, specifically, intrafollicular delivery of active molecules has become a preferred approach in recent years. A study by Fresta and Puglisi suggested that stratum corneum lipid-based unilamellar liposomes may be suitable devices for dermal delivery of drugs. Fresta and Puglisi. 1996. J.Drug Target 4: 95-101. Of great interest is the recent development of ultradeformable liposomes that have been used to deliver a variety of small and large molecules to the skin. For example, vesicles containing phosphatidylcholine mixed with edge activators such as sodium cholate, Span 80 and Tween 80 were successfully used for the delivery of the hormone oestradiol. El Maghraby et al. 2000. Int.J.Pharm. 196: 63-74. Cevc. 1996. Crit.Rev.Ther.Drug Carrier Syst. 13: 257-388. Particularly relevant are findings that cationic lipid-based formulations can deliver small and large molecules including oligonucleotides to the hair follicles. This delivery may have exquisite specificity since it takes place via the junction of the internal and external root sheath. Lieb et al. 1997. J.Pharm. Sci. 86: 1022-1029. Hoffman showed that phosphatidylcholine-based liposomes can target dyes, melanins, genes and proteins selectively to hair follicles. Hoffman. 1998. J.Drug Target 5: 67-74. Genes delivered are active in the follicle, making the follicle a target for selective gene therapy. Li and Hoffman. 1995. Nat.Med. 1: 705-706. Hoffman. 2000. Nat. Biotechnol. 18: 20-21.

Dosage and Administration of Chemical Inducer

In the practice of the present invention, a composition comprising a chemical inducer is applied to the scalp of a patient or the skin of a nonhuman mammal prior to exposure of the patient or the mammal to a cytotoxic, chemotherapeutic agent. In order to protect hair follicle cells against killing by the chemotherapeutic agent, the chemical inducer must reach a concentration in the hair follicles that is sufficiently high to activate the stress protein response in the follicle cells, which results in an objectively measurable increase in the concentration of at least one stress protein selected from the group consisting of Hsp90, Hsp70, Hsp25-27 and P-glycoprotein. More preferably, the levels of several or all of these stress proteins are elevated. An increase of about 25% in the concentration of a stress protein is readily detectable by western blot analysis using an antibody against the stress protein. While the ranges of concentrations that cause a detectable stress protein response in mammalian cell cultures are known for many chemical inducers (see, for example, Zou et al. 1998. Cell Stress & Chaperones 3: 130-141, incorporated herein by reference) and can serve as an initial guide for dose-finding studies, the concentrations required in compositions for topical administration to the scalp of a patient (or skin of another mammal) are preferably determined empirically for each composition. It will be appreciated that the inducer concentration reached in the hair follicles is dependent on the chemical properties of the inducer and on the efficacy of the chosen penetration enhancer, and can be determined for each chemical inducer and penetration enhancer by the skilled person as further described herein or by any other method known in the art. Standard clinical dose-finding studies may be carried out to predict by how much levels of stress proteins in hair follicles need to be increased for maximal protection of the cells against various chemotherapeutic drugs. The most relevant clinical parameter to be measured is hair density before and after chemotherapy. These measurements may be quantitative (hair count in a area of skin of defined size) or semiquantitative (estimating grades of alopecia). Alternatively or additionally, skin biopsies may be taken and analyzed for density and/or morphology of hair follicles. As an imperfect substitute endpoint (see before) activation of the stress protein response in hair follicle cells prior to administration of chemotherapeutic drug can be estimated in scalp biopsies by immunocytochemical methods (Hashizume et al. 1997. Int.J.Dermatol. 36: 587-592. Yu et al. 1999. J.Invest. Dermatol. 112: 370-375) or western blot using a stress protein antibody.

The time at which a composition comprising an inducer is best administered to the scalp of a patient (or skin of another mammal) relative to the time of initiation of a chemotherapy treatment cycle may also be determined empirically according to standard protocols. Kinetics of delivery of chemical inducer to the hair follicles will vary with the nature of the chosen inducer and penetration enhancer. In cell culture, exposure to a sufficient concentration of a chemical inducer results in a rapid activation of the stress protein response, and cytoprotective levels of stress proteins are reached within about 2-12 hours. As skin represents a significant barrier to delivery of molecules, attainment of cytoprotective levels of stress proteins in hair follicles may be delayed by up to 24 hours, depending on the nature of the chosen chemical inducer and penetration enhancer. Thus, a composition comprising a chemical inducer of the stress protein response may be administered between about 2 and 36 hours prior to administration of a chemotherapeutic agent. Preferably, a composition comprising a chemical inducer of the stress protein response will be administered between about 8 and 24 hours ahead of chemotherapy. Once cytoprotective levels of stress proteins are reached in the cells of the hair follicles, the hair follicles will retain an increased resistance to chemotherapeutic agents for typically 1-2 days. With this guidance, a person skilled in the art is enabled to empirically define with only routine experimentation an appropriate dosage and an appropriate regime of administration of a particular composition comprising a chemical inducer that provide effective protection of hair follicles against chemotherapeutic agents.

Dosage and Administration of Physical Inducer

In another aspect of the practice of the present invention, the scalp of a patient or the skin of a nonhuman mammal is exposed to a physical inducer of the stress protein response prior to exposure of the patient or the mammal to a cytotoxic, chemotherapeutic agent. In order to protect hair follicle cells against killing by the chemotherapeutic agent, the dose of physical inducer administered must be sufficiently high to activate the stress protein response in the follicle cells, which results in an objectively measurable increase in the concentration of at least one stress protein selected from the group consisting of Hsp90, Hsp70, Hsp25-27 and P-glycoprotein. More preferably, the levels of several or all of these stress proteins are elevated. An increase of about 25% in the concentration of a stress protein is readily detectable by western blot analysis using an antibody against the stress protein. A preferred physical inducer is heat. Heat may be delivered or produced in a target tissue by different means including direct contact with a heated surface or a heated liquid, ultrasound, infrared radiation, or microwave or radiofrequency radiation. For the practice of the invention, a preferred means of delivering heat to the scalp of a patient or the skin of a mammal involves direct contact with a heated liquid such as water. In a nonlimiting example, a patient is provided a device resembling a shower cap that covers the scalp of the patient. The cap extends slightly beyond the hairline of the patient and forms a watertight seal with the skin immediately adjacent to the hairline. The inside of the cap contains an appropriate volume of water or other physiological aequous solution that is in correspondance with a temperature-controlled waterbath by means of an appropriate inlet and outlet, valves, connecting tubes and a water pump. The range of heat doses that cause a detectable stress protein response in mammalian cell cultures is known and can serve as an initial guide for dose-finding studies. The typical range of elevated temperatures extends from about 39° C. to about 45° C., and the typical duration of elevated temperature exposures is between about 2 hours and 15 min. The appropriate heat doses to be applied to the scalp of a patient (or skin of another mammal) are preferably determined empirically. Standard clinical dose-finding studies may be carried out to predict by how much levels of stress proteins in hair follicles need to be increased for maximal protection of the cells against various chemotherapeutic drugs. The most relevant clinical parameter to be measured is hair density before and after chemotherapy. These measurements may be quantitative (hair count in a area of skin of defined size) or semiquantitative (estimating grades of alopecia). Alternatively or additionally, skin biopsies may be taken and analyzed for density and/or morphology of hair follicles. As an imperfect substitute endpoint (see before) activation of the stress protein response in hair follicle cells prior to administration of chemotherapeutic drug can be estimated in scalp biopsies by immunocytochemical methods (Hashizume et al. 1997. Int.J.Dermatol. 36: 587-592. Yu et al. 1999. J.Invest. Dermatol. 112: 370-375) or western blot using a stress protein antibody.

The time at which an appropriate heat dose is best administered to the scalp of a patient (or skin of another mammal) relative to the time of initiation of a chemotherapy treatment cycle may also be determined empirically according to standard protocols. In cell culture, exposure to a an appropriate heat dose results in a relatively rapid activation of the stress protein response, and cytoprotective levels of stress proteins are reached within hours rather than days. Thus, an appropriate heat dose may be administered between about 2 and 24 hours prior to administration of a chemotherapeutic agent. Preferably, the heat dose will be administered between about 6 and 12 hours ahead of chemotherapy. The latter time delays refer to initiation of chemotherapy treatment after initiation of heating. Once cytoprotective levels of stress proteins are reached in the cells of the hair follicles, the hair follicles will retain an increased resistance to chemotherapeutic agents for typically 1-2 days. With this guidance, a person skilled in the art is enabled to empirically define with only routine experimentation an appropriate heat dose and an appropriate regime of administration of the heat dose that provide effective protection of hair follicles against chemotherapeutic agents.

Animal Models of Chemotherapy Induced Alopecia

While imperfect stand-ins for the human patient, animal models of alopecia can be used to evaluate inducers and protection methods. Human hair growth appears to differ from that of many animals, in that in humans 90% of follicles are in the anagen phase, whereas in adult animals such as rodents this percentage is drastically lower. Two animal models that, with respect to growth phase, approach the human situation are newborn (8-day-old) rats (Hussein et al. 1990. Science 249: 1564-1566) and C57/BL/6 mice after depilation of a portion of the fur coat. Paus et al. 1990. Br. J. Dermatol. 122: 777-784. Paus et al. 1994. Am. J. Pathol. 144: 719-734. In the first model, advantage is taken of the active phase of hair growth in the newborn rats, and in the second model, hair regrowth is synchronized by depilation. In the mouse model, resting (telogen) hair follicles in the depilated skin of 6-8-week-old female C57BL/6 mice are induced to enter active hair growth (anagen). This is achieved by painting the entire back or a desired portion of the fur coat of anesthesized animals (30 mg/kg pentobarbital) with a wax and rosin mixture, which mixture is peeled off after hardening. Paus et al. 1990. Br. J. Dermatol. 122: 777-784. Schilli et al. 1998. J. Invest. Dermatol. 111: 598-604. Pharmacological compositions typically are administered topically about 5 days after depilation, at which time all hair follicles are in anagen III-IV of the hair cycle. Hence, a formulation containing a chemical inducer of the stress protein response) or a dose of a physical inducer such as heat will be administered at the latter time point. The two models were used extensively in studies of alopecia induced by chemotherapeutic drugs, including adriamycin and cyclophosphamide. Balsari et al. 1994. FASEB J. 8: 226-230. Schilli et al. 1998. J. Invest. Dermatol. 111: 598-604. Jimenez and Yunis. 1992. Cancer Res. 52: 413-415. The animal models may be used for proof-of-principle experiments, for evaluation of potential penetration enhancers concerning their ability to improve delivery of a chemical inducer to hair follicles, for estimation of the local toxicity of a chemical inducer, for a demonstration that localized delivery of a chemical inducer or local exposure to a physical inducer does not result in an elevated systemic concentration of the chemical inducer, in generalized activation of the stress protein response by the physical or chemical inducer, etc. The invention thus also comprises methods for identifying agents (i.e., chemical inducers or combinations of chemical inducers and penetration enhancers) for use in the protection of a human or animal from chemotherapy-induced alopecia comprising (a) administering a test agent to an animal model of chemotherapy-induced alopecia, and (b) determining whether said agent is capable of inducing the stress protein response in said animal model. Also encompassed are methods for identifying agents for use in the protection of a human or animal from chemotherapy-induced alopecia comprising (a) selecting an agent capable of inducing the stress protein response, and (b) administering said test agent to an animal model of chemotherapy-induced alopecia and determining whether said agent protects against chemotherapy-induced alopecia.

To further illustrate the invention, nonlimiting examples of experiments using the above-mentioned animal models of alopecia are described in the sections that follow.

A chosen pharmacological treatment or physical treatment (e.g., heat treatment) will need to be shown to induce the stress protein response in a majority of relevant cells of hair follicles. Further, it will be important for the optimization of a treatment regime to be able to assess the relative magnitude and duration of the induced stress protein response in hair follicles. For these purposes, an immunohistochemical assay will be utilized that estimates in cells of hair follicles and other cells of the skin levels of the major stress-inducible form of Hsp70. There are at least two valid reasons for the choice of inducible Hsp70 as a preferred indicator for the stress protein response. First, Hsp70 is one of the most abundant Hsps and was shown to be on its own cytoprotective. Liu et al. 1992. Cancer Res. 52: 3667-3673. Li et al. 1995. Exp. Cell Res. 217: 460-468. Second, it is clear from scores of previous studies using cell lines and animal tissues that expression of the major inducible form of Hsp70 is tightly regulated in rodents. Welch et al. 1983. J. Biol. Chem. 258: 7102-7111. In the absence of stress, its level is very low to absent in all cell lines and most tissues. During and subsequent to stress, the protein rapidly accumulates to a dramatically elevated level. A study by Hashizume et al. (Hashizume et al. 1997. Int. J. Dermatol. 36, 587-592) examined levels of inducible Hsp70 in the C57/BL/6 mouse and found that inducible Hsp70 expression in the anagen hair follicles is low. Only during the anagen-catagen transformation did the level of inducible Hsp70 increase significantly. A monoclonal antibody that specifically detects inducible Hsp70 in cultured rodent cells and in fresh and fixed tissue sections is commercially available (<<C92>>, StressGen Biotechnologies Corp., Victoria, BC (cat.#: SPA-810)).

Experiments to validate the immunohistochemical assay require that expression of Hsp70 is induced, since, as discussed before, this protein is normally absent or only present at a very low level. Two different methods can be used for induction of the Hsp70. The first involves exposing animals to whole body hyperthermia (by immersion in a waterbath). While optimal temperature and duration of the heat exposure would need to be determined experimentally, previous cell culture experiments provide sufficient initial guidance for at least achieving, without further experimentation, a level of induction of Hsp70 that is detectable immunohistochemically. The second method is based on previous observations by Li and Hoffman. Li and Hoffman. 1995. Nat. Med. 1: 705-706. These researchers found that liposomes containing a CMV promoter-controlled β-galactosidase gene were efficiently and selectively delivering the β-galactosidase gene to mitotically active cells (matrix cells and presumptive follicle stem cells) of mouse anagen hair follicles, where the gene was actively expressed. The same protocol can be used for introducing into follicle cells an expression construct for an activated human HSF1 (mutant HSF1d202-316, referred to hereinafter as HSF1(+)). HSF1(+) is known to strongly enhance expression of inducible Hsp70 in different cell types. Xia et al. 1999. Cell Stress & Chaperones 4: 8-18.

For assay validation experiments newborn rats and adult mice after depilation of a portion of their fur coat are exposed to moderately severe whole body hyperthermia. Alternatively or additionally, liposomes containing a CMV promoter-driven hsf1(+) gene or, as a control, a β-galactosidase gene are administered to areas on the backs of newborn rats or depilated areas of adult mice. After an appropriate time (6-48 h after heat exposure, or 1, 3 or 5 days after transduction), treated and untreated animals are sacrificed, and skin samples are taken. These samples can be processed using a standard immunohistochemistry protocol. To provide an example protocol, the skin samples can be embedded in O.T.C. (Miles) and quick-frozen. Yu et al. 1999 J. Invest. Dermatol. 112: 370-375. Frozen specimens can be sectioned on a cryostat (5 um) and collected on clean, charged slides. Subsequent to air-drying and fixation in acetone, slides can be washed, blocked and exposed to Hsp70 antibody C92. C92 antibody on the specimens can be detected with an appropriate enzyme-labeled secondary antibody. Alternatively, if necessary because of high background, a biotinylated C92 antibody (commercially available) may be used to eliminate the need for secondary antibody.

It is noted that specific nucleic acid hybridization could be used as an alternative assay of increased hsp70 gene expression in the unlikely event that antibody binding proves unsuccessful. Rat and mouse hsp70 genes were cloned (Perry et al. 1994. Gene 146: 273-278. Longo et al. 1993. J. Neurosci. 36: 325-335), and hybridization probes could, therefore, readily be prepared.

As was also discussed before, over the last ten years it became clear that preferential and efficient delivery of small molecular weight drug substances as well as large molecules such as nucleic acids and proteins to mitotically active cells of hair follicles can be achieved by topical administration of lipid-based formulations and liposomes containing the active substance of interest. Balsari et al. 1994. FASEB J. 8: 226-230. Li and Hoffman. 1995. Nat. Med. 1: 705-706. Lieb et al. 1992. J. Invest. Dermatol. 99: 108-113. Lieb et al. 1997. J. Pharmaceutical Sciences 86: 1022-1029. Li et al. 1993. In Vitro Cell. Dev. Biol. 29A: 192-194. Li et al. 1993. In Vitro Cell. Dev. Biol. 29A: 258-260. Li and Hoffman. 1995. In Vitro Cell. Dev. Biol. 31A: 11-13. Hoffman. 1997. J. Drug Targeting 5: 67-74. Foldvari et al. 1999. Biotechnol. Appl. Biochem. 30: 129-137. For liposomes it was further shown that there is only negligible release of drug substance into the circulation. Balsari et al. 1994. FASEB J. 8: 226-230. Li and Hoffman 1997. J. Derm. Sci. 14: 101-108. In the present example experiments liposomal formulations as described by the Hoffman group (Hoffman. 1997. J. Drug Targeting 5: 67-74) are used to deliver to hair follicle cells drug substances (chemical inducers) that induce the stress protein response. Hoffman's liposomes for small molecules and proteins were phosphatidylcholine-based, and those for nucleic acids contained either phosphatidylcholine alone or phosphatidylcholine: cholesterol: phosphatidylethanolamine in a 5:3:2 ratio.

In the example experiments two types of chemical inducers of the stress protein response are tested (individually), small molecule compound sodium arsenite and HSF1(+). HSF1(+) can be delivered as a nucleic acid encoding HSF1(+) or as recombinant protein. The nucleic acid can be a plasmid vector containing an hsf1(+) gene under the control of a constitutively active cytomegalovirus (CMV) promoter. In a therapeutic setting it will be desirable that the stress protein response is only induced transiently. Although the plasmid-borne hsf1(+) gene will be inactivated with time, this inactivation may be considered too slow. An alternative would be to use a different (eukaryotic) expression vector that will allow for regulated expression of the hsf1(+) gene. Gene switches that are activated/repressed by presumptively innocuous small molecular weight substances (e.g., tetracycline, RU486, etc.) are known and are readily available. Gossen et al. 1996. Science 268: 1766-1769. Gossen and Bujard. 1992. Proc. Natl. Acad. Sci. USA 89: 5547-5551. Wang et al. 1997. Nat. Biotechnol. 15: 239. Wang et al. 1997. Gene Therapy 4: 432-441. The latter issue does not arise if HSF1(+) is delivered as a recombinant protein. When wildtype human HSF1 and HSF1(+) were expressed from similar constructs in mammalian cells, wildtype HSF1 accumulated to a significantly higher level than HSF1(+) (unpublished data), suggesting that the mutant protein (i.e., HSF1(+)) is considerably less stable than the wildtype protein. Subsequent experiments estimated the half life of HSF1(+) to be 6-8 hours. Thus, introduction into cells of recombinant HSF1(+) can only produce a transient induction of the stress protein response. HSF1(+) can be produced, for example, as a FLAG-tagged protein or as a glutathione transferase fusion in E.coli. Voellmy. 1996. In Stress-Inducible Cellular Responses, U. Feige, R. I. Morimoto, I. Yahara, and B. S. Polla, eds. (Basel: Birkhaeuser Verlag). pp. 121-137. Guo, Y., Guettouche, T., Fenna, M., Boellmann, F., Pratt, W. B., Toft, D. O., Smith, D. F., and Voellmy, R. Unpublished data. FLAG-tagged HSF1 (+) and the glutathione transferase fusion protein can be purified by affinity chromatography methods. The glutathione transferase moiety can be cleaved off during purification, yielding HSF1(+). Because it does not prevent HSF1(+) function (unpublished result), removal of the tag from FLAG-tagged HSF1 may not be considered necessary. Essentially pure recombinant proteins can be obtained. It is noted that because of the relative instability of HSF1(+) it will be advantageous to use a production strain that is low in proteolytic activity. While HSF1(+) may be expressed in bacterial expression systems, it may also be expressed in and purified from eukaryotic expression systems, including baculovirus-infected insect cells.

Sodium arsenite is dissolved in water or phosphate-buffered saline at or near maximal solubility. HSF1(+) protein or nucleic acid is dissolved at the highest practical concentration. These solutions and series of dilutions are then incorporated into liposomes as described by Hoffman. Hoffman. 1997. J. Drug Targeting 5: 67-74. Controls include empty liposomes and liposomes containing a protein or nucleic acid unrelated to HSF1(+), respectively. These liposomal preparations are administered to areas on the back, side or abdomen of newborn rats (8-day-old) or depilated areas of adult mice (5 days after depilation). Administration may be once or may be repeated at appropriate (e.g., daily) intervals. At different times (12 hours, 1-10 days) after the last administration, animals are sacrificed. Skin samples are taken, and sections are prepared and analyzed by the immunohistochemical assay described before as well as microscopically to estimate density and morphology of hair follicles.

These experiments can answer several questions. Estimates can be obtained for each chemical inducer of the minimal and best concentrations to induce the stress protein response as well as of the maximal concentration at which inducer can be administered without causing damage to hair follicles (only relevant for sodium arsenite). Regarding the latter information, the reader may be reminded that the stress protein response is induced in response to a marginal proteotoxic stress. Thus, at excessive concentrations a chemical inducer such as sodium arsenite will have significant cytotoxicity and will kill hair follicle cells. For this reason it is critical to determine ranges of concentrations at which the chemical inducer triggers Hsp overexpression without causing irreversible damage. An excessive concentration of inducer can be detected by a diminished stress protein response compared to that induced by a lower concentration as well as by changes in the morphology and density of hair follicles.

Second, the experiments can show whether the liposomal preparations target all or nearly all hair follicle matrix cells (and putative follicle stem cells). If inducer-containing liposomes prepared according to the directions provided by Hoffman (Hoffman. 1997. J. Drug Targeting 5: 67-74) are found to target only a small fraction of mitotically active matrix and putative stem cells, analogous experiments to those described above can be carried out to test liposomes of different composition or other penetration enhancers.

Third, the experiments define, for each inducer, the time course of activation of the stress protein response as well as its persistence. This information is required for the design of effective alopecia prevention regimes in the animal models. Optimal protection will only result if chemotherapeutic drugs are administered after activation of the stress protein response occurred and Hsp concentrations increased to appropriately elevated levels. Note that the data obtained from the above experiments only define a minimum delay between pretreatment with inducer and treatment with chemotherapeutic drug, i.e., they will only provide initial conditions for the experiments described below. It will be the latter experiments that define the level of inducible Hsp70 that correlates with optimal protection against alopecia induced by a chemotherapeutic agent. Data on the persistence of the stress protein response allow for an estimation of whether one-time induction of the response is likely to provide protection for the entire period during which a chemotherapeutic agent is expected to be present at an effective concentration. In addition, they provide information on whether induced levels of Hsps persist for a sufficiently long time to be potentially protective in animals subjected to regimes involving multiple administration of a chemotherapeutic drug. Finally, they reveal whether sequential administration of several doses of inducer-containing liposomes effectively prolongs the period during which concentrations of Hsps are elevated.

Fourth, the experiments can also reveal whether repeated administration of inducer-containing liposomes will, in addition to extending the duration of the stress protein response, produce a more pronounced response and/or increase the fraction of matrix and putative stem cells of hair follicles that mount a stress protein response.

Model Experiments for Establishing Conditions for Optimal Protection of Hair Follicles Against Selected Chemotherapeutic Agents The following experiments can establish the conditions that result in optimal protection of hair follicles against different chemotherapeutic agents in the animal models. Although chemotherapeutic agents are frequently used in combination, animals will only be exposed to single drugs in these experiments. Because questions relating to the relative importance of an individual drug in a particular combination are avoided, this simplification allows for a conclusive demonstration that induction of the stress protein response protects against hair follicle toxicity of a particular drug. The experiments described below concentrate on several drug substances that produce severe alopecia in humans and that are present in many of the commonly used therapeutic combinations. Selected chemotherapeutic drugs are cyclophosphamide, adriamycin, taxol, etoposide and vincristine.

In initial experiments, conditions are established under which single intraperioneal injections of the different selected chemotherapeutic agents cause severe alopecia (grade 3, characterized by essentially complete failure of hair growth/regrowth in most animals; see below). Previous studies can provide valuable guidance. For example, induction of alopecia in newborn rats by adriamycin and cyclophosphamide was described by Hussein et al. (Hussein et al. 1990. Science 249: 1564-1566), Jimenez and Yunis (Jimenez and Yunis. 1992. Cancer Res. 52: 5123-5125), Balsari et al. (Balsari et al. 1994. FASEB J. 8: 226-230) and Jimenez et al. (Jimenez et al. 1995. Am. J. Med. Sci. 310: 43-47), and by etoposide by Davis et al. (Davis et al. 2001. Science 291: 134-137). Alopecia in the C57/BL/6 mouse model resulting from exposure to cyclophosphamide was studied by Paus and collaborators. Paus et al. 1994. Am. J. Pathol. 144: 719-734. Schilli et al. 1998. J. Invest. Dermatol. 111: 598-604. Other researchers described alopecia in mice following administration of adriamycin. Malkinson et al. 1993. J. Invest. Dermatol. 101: 135S-137S. D'Agostini et al. 1998. Int. J. Oncol. 13: 217-224. To obtain results that are statistically meaningful, groups consisting of minimally ten animals for each data point are used in these and subsequent experiments. The primary assay for alopecia is macroscopic evaluation performed independently by two observers. Four grades are distinguished: grade 0: no alopecia, grade 1: mild alopecia defined as less than 50% hair loss, grade 2: moderately severe alopecia defined as more than 50% hair loss, and grade 3 with total or virtually total (>90%) alopecia. Hussein et al. 1990. Science 249: 1564-1566. Sredni et al. 1996. Int. J. Cancer 65: 97-103. Corroboration of findings can be obtained from microscopic examination of skin sections, which examination assesses density and morphology of hair follicles. Note that, at least in the mouse model, increased pigmentation and skin thickness are known to be correlated with anagen progression (explained in Paus et al. 1990. Br. J. Dermatol. 122: 777-784). Thus, should the need arise, estimation of skin pigmentation and thickness could serve as substitute assays of hair growth. These initial experiments define, for each chemotherapeutic agent, the optimal concentration at which virtually complete alopecia is produced, the location on the animals' body in which the alopecia phenotype is most readily observed (Experiments will be conducted with mice depilated dorsally, laterally and ventrally.), the time after administration at which expression of the phenotype is most readily evaluated as well as the reproducibility of the expression of the phenotype. Note that in order to keep experimental protocols as simple as possible, single administration of chemotherapeutic agents is highly preferred.

To assess and optimize protective effects of an activated stress protein response against alopecia induced by a chemotherapeutic agent, groups of at least ten 8-day-old rats or C57/BL/6 mice 5 days after depilation are treated topically (once or repeatedly as indicated) with liposomal preparations containing a chosen inducer (here sodium arsenite and HSF1 (+)) of the stress protein response. Three different preparations are tested, the first containing inducer at the lowest concentration at which it triggers a measurable increase of the level of inducible Hsp70 after 12 or 24 hours (as estimated in the experiments described earlier), and the second and third containing successively higher concentrations. Administration of a chemotherapeutic agent occurs either 12 or 24 hours after (last) administration of inducer-containing liposomes or about 12 hours or 24 hours later. A predetermined amount of a chemotherapeutic agent (defined in the preceding paragraph) is injected intraperitoneally into all inducer-treated animals and a group of mock-treated (with empty liposomes in experiments using sodium arsenite or with liposomes containing a control protein or nucleic acid in experiments using HSF1(+) protein or gene) animals. Additional inducer- and mock-treated groups are injected with vehicle only. Alternatively, to assess and optimize protective effects of an activated stress protein response against alopecia induced by physical inducer heat, groups of at least ten 8-day-old rats or C57/BL/6 mice 5 days after depilation are treated topically (once or repeatedly as indicated) are subjected to local heat treatments of different intensity (heat exposure form 39 to 45° C. for 15 to 120 min) or are left untreated. Local heat treatment may be administered by several different procedures. A simple procedure may involve placing an anesthesized animal on an indented metal mesh fixed to a waterbath in such a way that the indented portion of the mesh and, consequently, the part of the animal's body resting in this indented portion are immersed in water. Administration of a chemotherapeutic agent may occur either 12 or 24 hours after (last) administration of a heat dose. A predetermined amount of a chemotherapeutic agent (defined in the preceding paragraph) is injected intraperitoneally into all groups of animals.

Animals are then returned to quarters, and, at the time previously identified as optimal for the assessment of the alopecia phenotype, grades of alopecia in all animals is recorded. The animals are then sacrificed, and skin samples are taken, fixed and sectioned. Sections are examined microscopically for hair follicle density and morphology. To confirm stress protein induction, several additional animals can be included in each group. These animals are sacrificed at the time of administration of the chemotherapeutic agent, and skin samples are taken and processed for immunohistochemical estimation of the level of inducible Hsp70, i.e., of the degree of induction of the stress protein response achieved.

For experiments in which alopecia is evaluated, individual animals are assigned an alopecia score ranging from 0 to 3 (see above). Alopecia scores for each treatment group are summarized by calculating the mean and standard deviation of alopecia scores of individual animals. Treatment groups are compared by one-way analysis of variance (ANOVA). If differences among treatment groups are detected by ANOVA, a post-hoc test (e.g., Scheffe's test or Student Newman Keuls test) can be used to determine which groups are different from each other. The criterion for statistical significance is a $p<0.05$.

To avoid possible systemic/organ toxicity of chemical inducers as well as impairment of the therapeutic efficacy of chemotherapeutic agents which would result if the stress protein response were also induced in cells of tumors to be treated, the above-described experiments used topically applied liposomal formulations to specifically deliver chemical inducers of the stress protein response to the relevant cells of hair follicles. Because of this topical delivery, only the latter cells but not other cells including the tumor cells targeted by the chemotherapy treatment should be protected against toxicity from the chemotherapeutic agents. Based on the previous reports cited above, topical administration of liposomal formulations of chemical inducers can be expected to result in the desired highly localized delivery of the inducers. Although small amounts of a chemical inducer such as sodium arsenite may end up in the circulation, its concentration will be minimal due to dilution and, because it will be far below the required threshold concentration, it will be incapable of activating the stress protein response systemically. Similarly, the systemic concentration of HSF1(+) is expected to be exceedingly low, and activation of the stress protein response in blood cells and organs should occur at most in only a few isolated cells. Note that the above discussion does not apply to treatment approaches in which a therapeutic stress protein response is induced by localized heat treatment.

In an experiment aimed at ascertaining that topically administered chemical inducers do not accumulate in the circulation and in major organs to levels that are sufficient for the induction of the stress protein response, animals are administered a liposomal formulation containing chemical inducer (sodium arsenite or a form of HSF1(+)) in an amount and under conditions known from previous experiments to be effective in preventing alopecia caused by chemotherapeutic drugs and, after an appropriate delay, injected with a chemotherapeutic drug. Controls are animals treated similarly but with empty liposomes and liposomes containing a control protein or nucleic acid, respectively. To estimate the contributions of the chemotherapeutic agent and the lipid components of the liposomes to induction of the stress protein response, further controls can include animals that did not receive chemotherapeutic agent (vehicle-injected) or were not pretreated with chemical inducer-containing or control liposomes. At various times prior to and subsequent to the time of administration of chemotherapeutic drug, animals are sacrificed and dissected. Extracts of PBL, heart, lung, brain, liver and kidney are prepared using routine methodology and are analyzed by western blot probed with antibody against inducible Hsp70 (C92). Levels of inducible Hsp70 are compared. As discussed before, this experiment is strongly expected to show induction of the stress response to be localized to cells of hair follicles.

The above disclosure cites numerous references. All publications, patents and patent applications cited herein are expressly incorporated herein by reference. While the invention has been described herein with reference to specific features, aspects and embodiments, it will be appreciated that the scope of the invention is not thus limited, but rather extends to and encompasses other variations, modifications and other embodiments. Accordingly, the invention is to be correspondingly interpreted as including all such variations, modifications and other embodiments within its spirit and scope as hereinafter claimed.

The invention claimed is:

1. A method of reducing chemotherapy-induced alopecia in a human patient or a mammalian animal to be subjected to chemotherapy treatment of a tumor not residing in the scalp or other region susceptible to chemotherapy-induced alopecia of the patient or the skin of the mammalian animal against chemotherapy-induced alopecia comprising:
   a) administering a heat dose that causes an increase in the concentration of at least one stress protein selected from the group consisting of Hsp90, Hsp70, Hsp25-27 and P-glycoprotein in hair follicles residing in skin or scalp that is exposed to the heat dose and that produces an increased resistance of the hair follicles to chemotherapeutic drugs in the scalp or other region susceptible to chemotherapy-induced alopecia of a human patient or the skin of a mammalian animal; and
   b) administering a chemotherapeutic drug to said human patient or said mammalian animal, wherein said heat dose is administered to the scalp of a human patient or the skin of a mammalian animal at a temperature of about 39-45° C. for about 15-120 minutes and said chemotherapeutic drug is administered between about 2 hours and 24 hours after said heat dose is administered.

2. The method according to claim 1, wherein the heat dose is administered by a means selected from the group consisting of direct contact with heated surface or liquid, infrared radiation, microwave radiation, ultrasound and radiofrequency radiation.

3. The method according to claim 2, wherein the heat dose is administered by direct contact with a heated surface.

4. The method according to claim 2, wherein the heat dose is administered by direct contact with a heated liquid.

5. The method according to claim 2, wherein the heat dose is administered by an infrared radiation.

6. The method according to claim 2, wherein the heat dose is administered by microwave radiation.

7. The method according to claim 2, wherein the heat dose is administered by ultrasound.

8. The method according to claim 2, wherein the heat dose is administered by radiofrequency radiation.

9. A method for protecting a human patient or a mammalian animal to be subjected to chemotherapy treatment of a tumor not residing in the scalp or other region susceptible to chemotherapy-induced alopecia of the patient or the skin of the animal against chemotherapy-induced alopecia, the protective method comprising administering a heat dose to the scalp or other region susceptible to chemotherapy-induced alopecia of the human patient or the skin of the animal whereby hair follicles in the scalp or other region susceptible to chemotherapy-induced alopecia of the patient or the skin of the animal are heated to and maintained at a temperature of about 39-45° C. for about 15-120 minutes and administering a chemotherapeutic drug to said human patient or mammalian animal between about 2 hours and 24 hours after said heat dose is administered.

10. The method of claim 9, wherein the heat dose is administered by a means selected from the group consisting of direct contact with heated surface or liquid, infrared radiation, microwave radiation, ultrasound and radiofrequency radiation.

11. The method according to claim 10, wherein the heat dose is administered by direct contact with a heated surface.

12. The method according to claim 10, wherein the heat dose is administered by direct contact with a heated liquid.

13. The method according to claim 10, wherein the heat dose is administered by an infrared radiation.

14. The method according to claim 10, wherein the heat dose is administered by microwave radiation.

15. The method according to claim 10, wherein the heat dose is administered by ultrasound.

16. The method according to claim 10, wherein the heat dose is administered by radio frequency radiation.

17. A method for protecting a human patient or a mammalian animal to be subjected to chemotherapy treatment of a tumor not residing in the scalp or other region susceptible to chemotherapy-induced alopecia of the patient or the skin of the animal against chemotherapy-induced alopecia, the protective method comprising administering a heat dose to the scalp or other region susceptible to chemotherapy-induced alopecia of the patient or the skin of the animal, wherein the effective heat dose is a dose equal to or greater than that required to cause an increase in the concentration of a stress protein selected from the group consisting of Hsp90, Hsp70, Hsp25-27 and P-glycoprotein in cells of hair follicles and administering a chemotherapeutic agent to said human patient or said mammalian animal, wherein said hair follicles of the scalp of said human patient or the skin of said mammalian animal is heated at about 39-45° C. for about 15-120 minutes and said chemotherapeutic drug is administered between about 2 hours and 24 hours after said heat dose is administered.

18. The method according to claim 17, wherein the heat dose is administered by a means selected from the group consisting of direct contact with heated surface or liquid, infrared radiation, microwave radiation, ultrasound and radiofrequency radiation.

19. The method according to claim 18, wherein the heat dose is administered by direct contact with a heated surface.

20. The method according to claim 18, wherein the heat dose is administered by direct contact with a heated liquid.

21. The method according to claim 18, wherein the heat dose is administered by an infrared radiation.

22. The method according to claim 18, wherein the heat dose is administered by microwave radiation.

23. The method according to claim 18, wherein the heat dose is administered by ultrasound.

24. The method according to claim 18, wherein the heat dose is administered by radiofrequency radiation.

25. A method for reducing chemotherapy-induced alopecia in a human patient or a mammalian animal to be subjected to chemotherapy treatment of a tumor not residing in the scalp or other region susceptible to chemotherapy-induced alopecia comprising administering a heat dose to the scalp or other region susceptible to chemotherapy-induced alopecia of the human patient or the skin of the animal whereby hair follicles in the scalp or other region susceptible to chemotherapy-induced alopecia of the patient or the skin of the animal are heated to and maintained at a temperature of about 39-45° C. for about 15-120 minutes and administering a chemotherapeutic drug to said human patient or mammalian animal between about 2 hours and 24 hours after said heat dose is administered.

26. The method according to claim 25, wherein the heat dose is administered by a means selected from the group consisting of direct contact with heated surface or liquid, infrared radiation, microwave radiation, ultrasound and radiofrequency radiation.

27. The method according to claim 26, wherein the heat dose is administered by direct contact with a heated surface.

28. The method according to claim 26, wherein the heat dose is administered by direct contact with a heated liquid.

29. The method according to claim 26, wherein the heat dose is administered by an infrared radiation.

30. The method according to claim 26, wherein the heat dose is administered by microwave radiation.

31. The method according to claim 26, wherein the heat dose is administered by ultrasound.

32. The method according to claim 26, wherein the heat dose is administered by radiofrequency radiation.

* * * * *

UNITED STATES PATENT AND TRADEMARK OFFICE
CERTIFICATE OF CORRECTION

PATENT NO. : 7,405,080 B2 Page 1 of 1
APPLICATION NO. : 09/939161
DATED : July 29, 2008
INVENTOR(S) : Richard W. Voellmy It is certified that error appears in the above-identified patent and that said Letters Patent is hereby corrected as shown below:

Column 11,
Line 37, "being thought by" should read --being treated by--.

Column 12,
Line 35, "acetaninophen" should read --acetaminophen--.

Column 16,
Line 43, "in a area of skin" should read --in an area of skin--.
Line 58, "to a an appropriate" should read --to an appropriate--.

Column 22,
Line 21, "morpohology" should read --morphology--.

Signed and Sealed this

Second Day of December, 2008

JON W. DUDAS
*Director of the United States Patent and Trademark Office*